(12) United States Patent
O'Brien

(10) Patent No.: US 7,908,018 B2
(45) Date of Patent: Mar. 15, 2011

(54) FLEXIBLE ELECTRODE

(75) Inventor: David O'Brien, Norcross, GA (US)

(73) Assignee: CardioMEMS, Inc., Atlanta, GA (US)

( * ) Notice: Subject to any disclaimer, the term of this patent is extended or adjusted under 35 U.S.C. 154(b) by 165 days.

(21) Appl. No.: 11/516,172

(22) Filed: Sep. 6, 2006

(65) Prior Publication Data

US 2008/0058912 A1 Mar. 6, 2008

(51) Int. Cl.
*A61N 1/00* (2006.01)
*A61B 5/04* (2006.01)

(52) U.S. Cl. .................. 607/152; 600/372; 600/393

(58) Field of Classification Search .................. 600/372, 600/393
See application file for complete search history.

(56) References Cited

U.S. PATENT DOCUMENTS

| | | | | |
|---|---|---|---|---|
| 5,010,895 A * | 4/1991 | Maurer et al. | | 607/138 |
| 5,161,533 A * | 11/1992 | Prass et al. | | 600/372 |
| 6,129,666 A * | 10/2000 | DeLuca et al. | | 600/372 |
| 6,210,339 B1 * | 4/2001 | Kiepen et al. | | 600/486 |
| 6,411,834 B1 * | 6/2002 | Nagai | | 600/348 |
| 6,892,086 B2 * | 5/2005 | Russell | | 600/372 |
| 6,973,706 B2 * | 12/2005 | Say et al. | | 29/595 |
| 7,206,630 B1 * | 4/2007 | Tarler | | 600/509 |
| 7,417,418 B1 * | 8/2008 | Ayliffe | | 324/71.1 |
| 2004/0010303 A1 * | 1/2004 | Bolea et al. | | 607/118 |
| 2006/0111626 A1 * | 5/2006 | Rossing et al. | | 600/372 |
| 2006/0183989 A1 * | 8/2006 | Healy | | 600/372 |

\* cited by examiner

*Primary Examiner* — Niketa I Patel
*Assistant Examiner* — Nicole F Lavert
(74) *Attorney, Agent, or Firm* — Ballard Spahr LLP

(57) ABSTRACT

An electrode array has a flexible body supporting a plurality of electrodes. Each electrode comprises an exposed connector pad at the upper end of the body, an exposed recording/stimulating pad at the lower end of the body, and a conductor located within the body and electrically connecting the connector pad and the recording/stimulating pad. In one embodiment the electrode array has an elongated recording/stimulating portion coiled or folded to distribute the exposed recording/stimulating pads in three dimensions. An implantation method employs an introducer with a helical portion to which an end of the flexible electrode is attached. The helical portion straightens to pass through a small-diameter cannula and then resumes its helical configuration to place the recording/stimulating portion of the attached electrode in a helix within the patient's tissues.

8 Claims, 19 Drawing Sheets

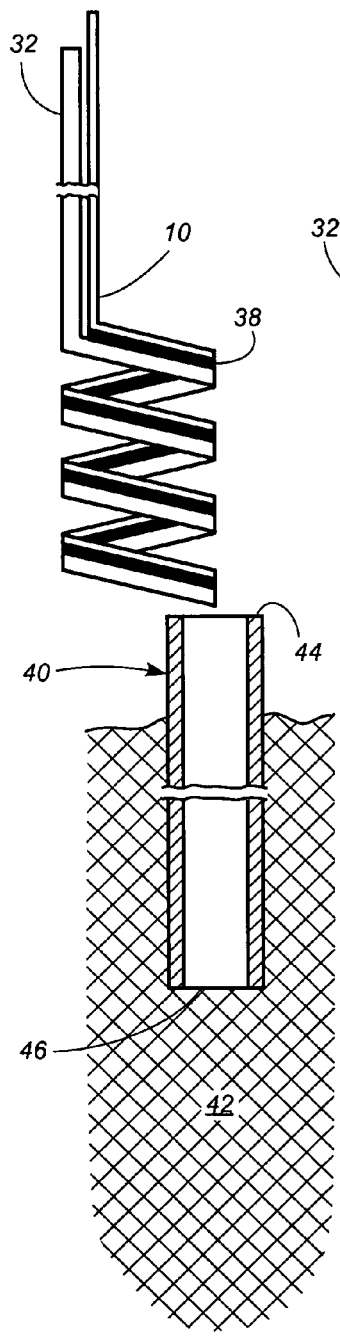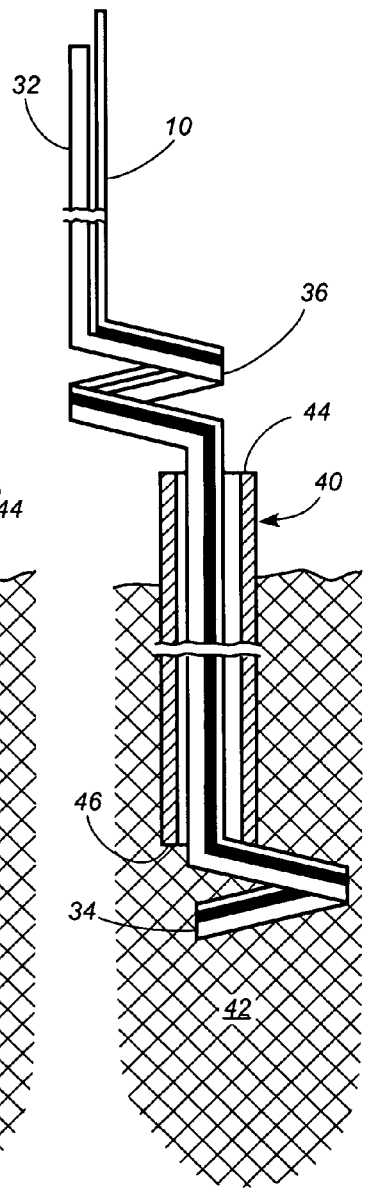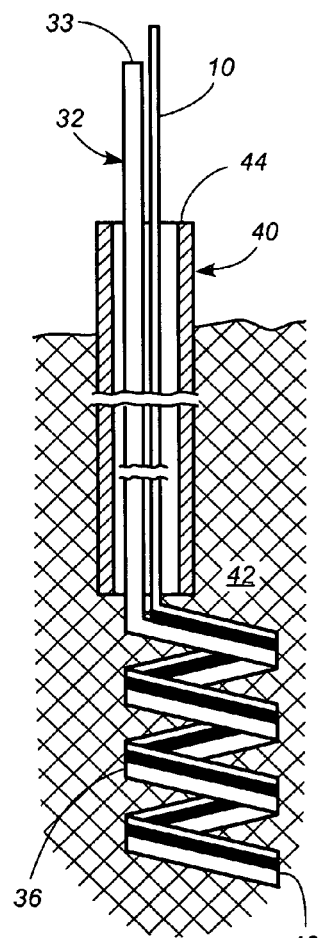
*Fig. 4*  *Fig. 5*  *Fig. 6*

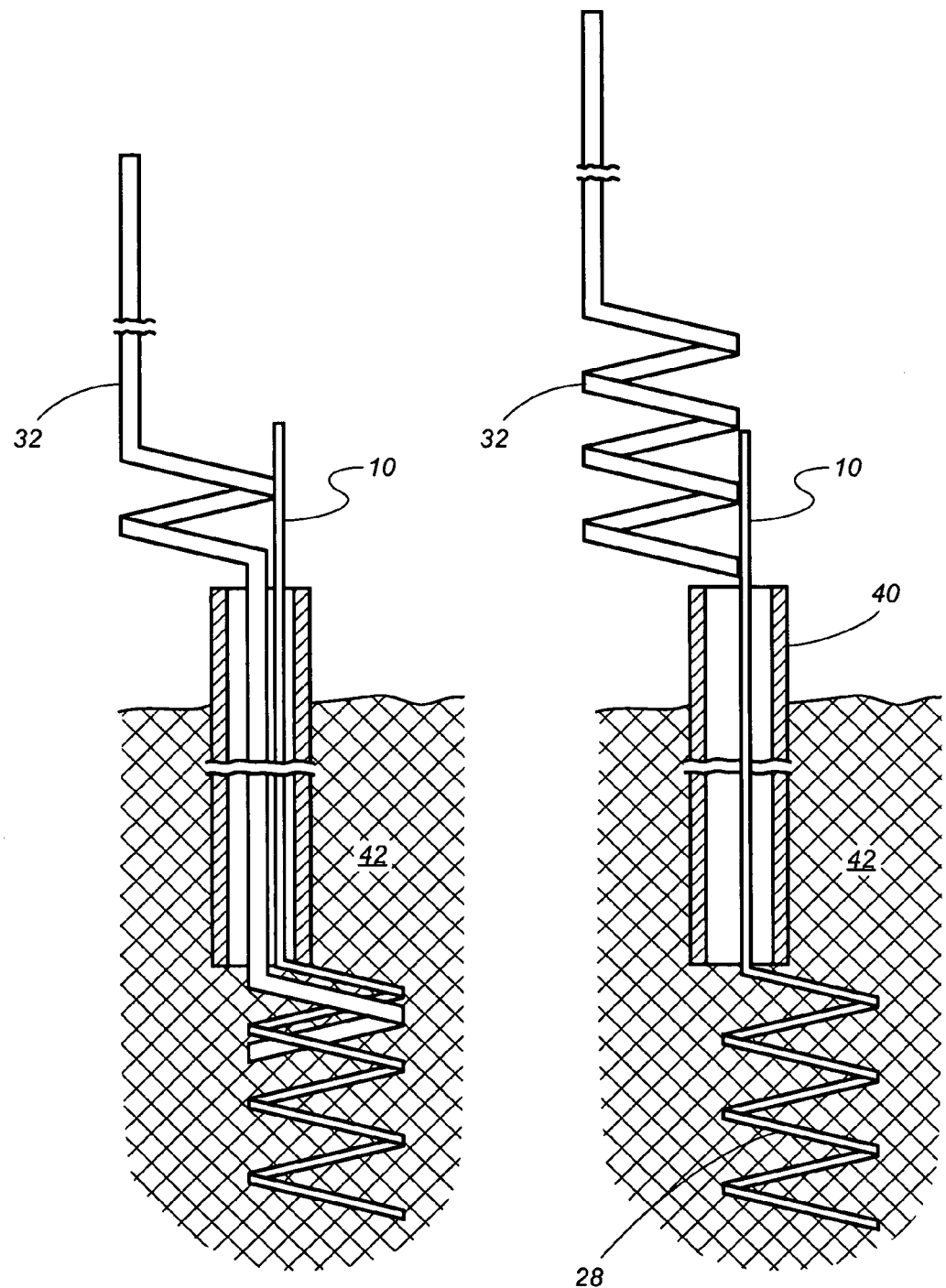
*Fig. 7*  *Fig. 8*

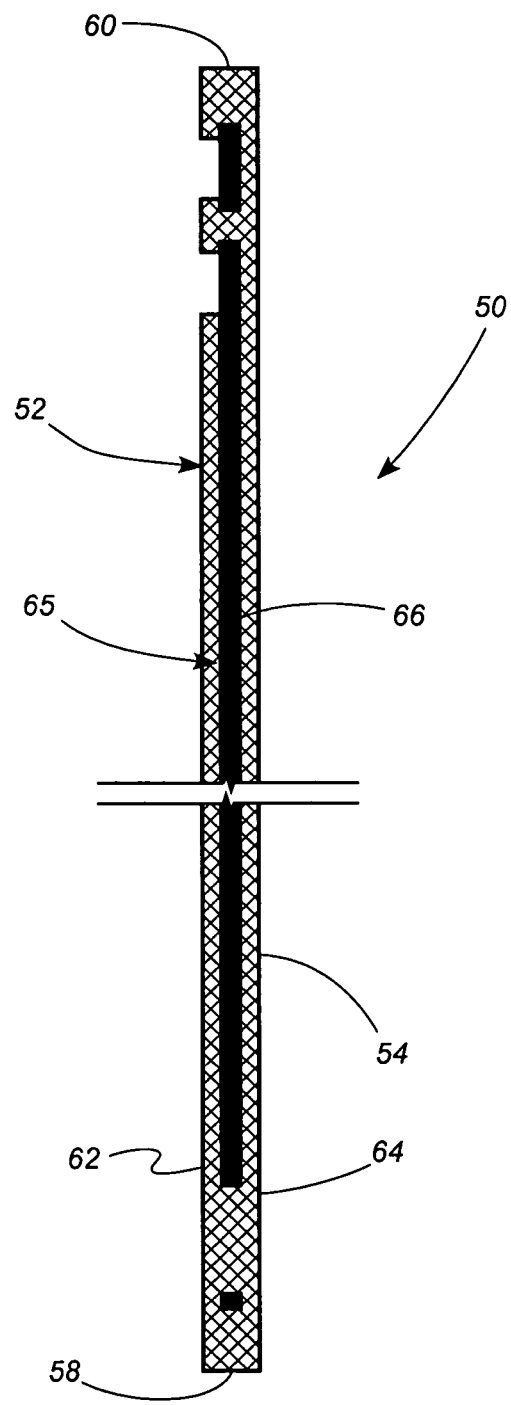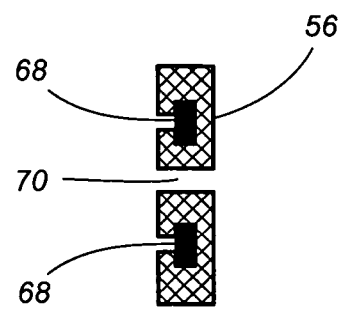
*Fig. 11*  *Fig. 12*

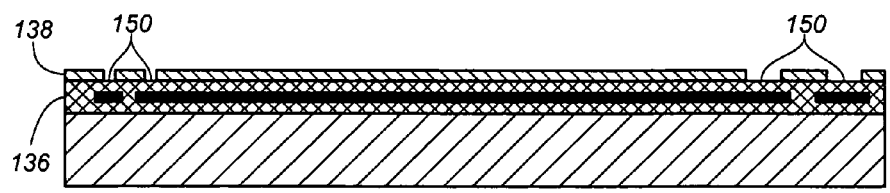
Fig. 34
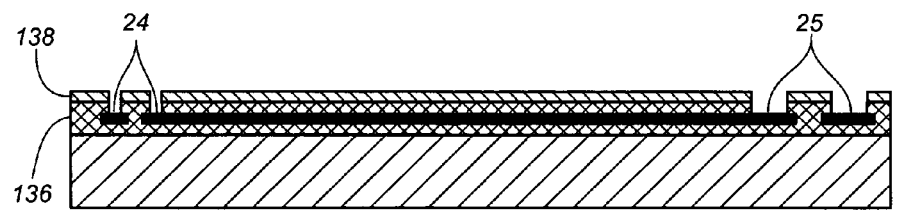
Fig. 35
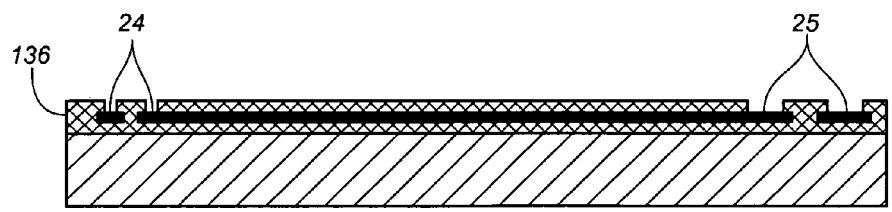
Fig. 36
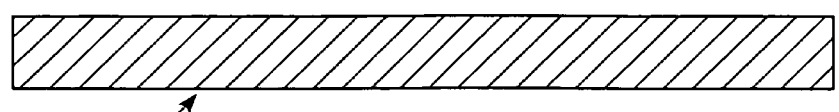
Fig. 37

FLEXIBLE ELECTRODE

TECHNICAL FIELD

This invention relates generally to electrodes for use within the body of a patient and to systems of manufacturing and of implanting such electrodes. More specifically, the invention relates to a flexible electrode that can create a distribution of electrode sites within the interior bulk of a tissue using only one penetration along a single electrode track.

BACKGROUND OF THE INVENTION

When used in medical applications, an electrode is an electrically conductive structure that either electrically stimulates or records the electrical activity of surrounding tissue within the body of a patient. Examples of medical applications for electrodes include deep brain stimulation and brain mapping. Deep brain stimulation electrodes have applications in the treatment of Parkinson's, epilepsy, chronic pain, depression, muscle spasticity, schizophrenia, anxiety, coma, addition, migraine, and Alzheimer's, among others.

Conventional medical electrodes present a number of disadvantages. First, known medical electrode arrays cannot be inserted into tissue without causing trauma to the tissue, a characteristic that is especially disadvantageous in the case of deep brain stimulation and brain mapping electrodes. Consequently, known electrode arrays can only be placed on the surface of the brain, making it impossible to stimulate or detect electrical activity below the surface of the brain without causing trauma to delicate brain tissue.

Second, known medical electrodes are typically denser than the tissue into which they are positioned. Thus any sudden acceleration or deceleration can cause movement of the electrode relative to the tissue, resulting in shearing or abrading of the surrounding tissue.

Third, known medical electrodes are typically less compliant than the surrounding tissue. Thus any mechanical vibration that results from energy input into the body will cause relative motion between the electrode and the surrounding tissue, again with the attendant risk of shearing or abrasion of the surrounding tissue.

Electrodes made to have a high degree of compliance are known. A problem with such structures is that they are limited in the manner in which they can interact with a particular tissue. More specifically, such highly flexible electrodes cannot be inserted into tissue because the flexible electrode itself does not have the necessary mechanical stiffness for it to be pushed into the cellular matrix of a given tissue. These devices can only be affixed to the surfaces of a tissue or inserted into a bodily organ that has a hollow cavity, such as the surface of the cochlear membrane, which will allow insertion of the flexible structure.

SUMMARY OF THE INVENTION

In a first aspect, the present invention comprises an electrode array having a substantially planar electrode body supporting one or more electrodes. Each of the electrodes comprises an electrode pad at its lower end, a connector pad at its upper end, and a conductor located within the body and electrically connecting the electrode pad and the connector pad. The body has an opening in registry with the electrode pad to the ambient and an opening in registry with the connector pad so as to expose the pads to the ambient.

In another aspect the invention comprises an electrode and an introducer for implanting the recording/stimulating section of the electrode into the tissues of a patient. The introducer has a helical lower portion. The lower end of the electrode is attached to the distal end of the introducer.

In a further aspect of the invention, introducer is used to implant the recording/stimulating section of the electrode into the tissues of a patient. The distal end of a cannula is inserted into the tissues of the patient. The distal end of the introducer is introduced into the cannula. The helical portion of the introducer unwinds to pass through the cannula and reforms into a helix as it exits the lower end of the cannula. The introducer pulls the recording/stimulating section of the electrode along with it to position it in a helical configuration within the tissues of the patient. The introducer is then detached from the electrode and extracted, leaving the electrode in place.

Objects, features, and advantages of the present invention will become apparent upon reading the following specification, when taken in conjunction with the drawings and the appended claims.

BRIEF DESCRIPTION OF THE DRAWINGS

FIGS. 4-8 are side views illustrating the use of the introducer of FIG. 3 to implant the electrode of FIG. 1 within the tissues of a patient.

FIG. 11 is a cross-sectional view of the electrode of FIG. 10 as seen along line 11-11 of FIG. 10.

FIG. 12 is a cross-sectional view of the electrode of FIG. 10 as seen along line 12-12 of FIG. 10.

FIGS. 21-37 are side views depicting a series of steps for manufacturing the electrode of FIG. 1.

DETAILED DESCRIPTION OF THE DISCLOSED EMBODIMENT

Figure 1:
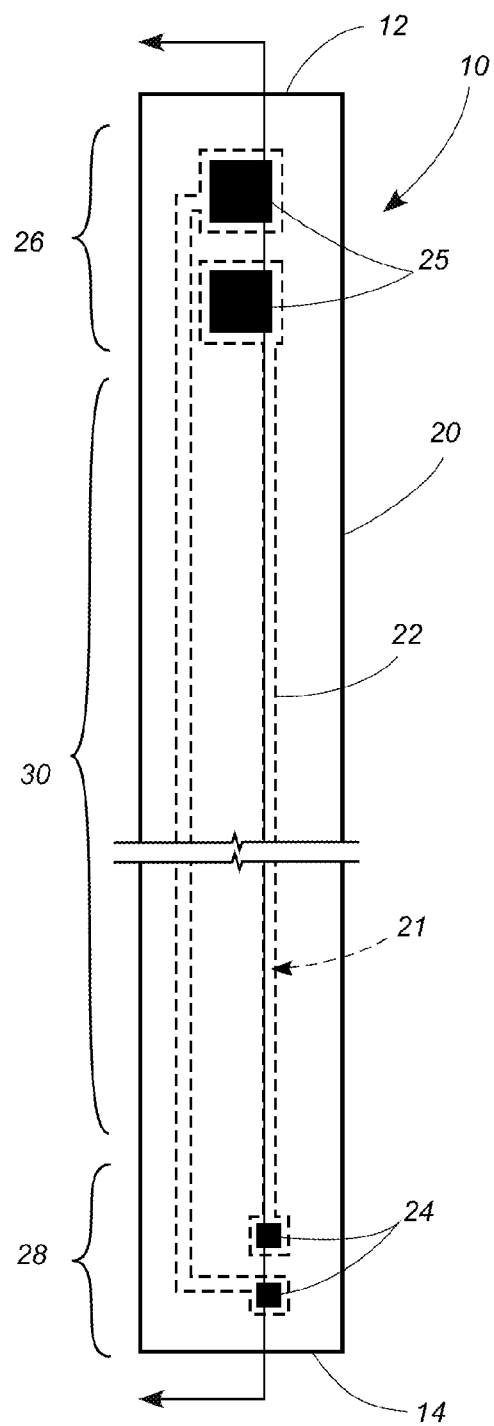
FIG. 1 is a side view of an electrode according to a first disclosed embodiment.
Figure 2:
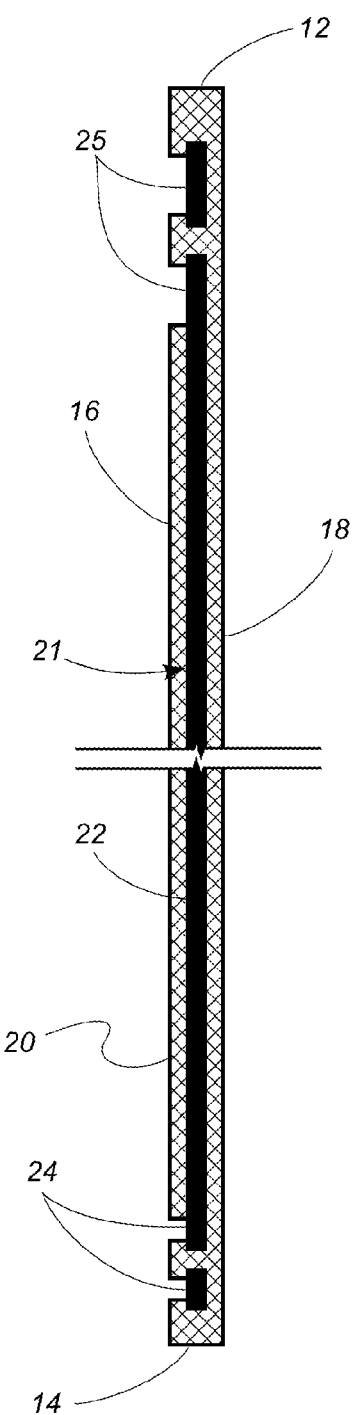
FIG. 2 is a cross-sectional view of the electrode of FIG. 1 as seen along line 2-2 of FIG. 1.

Referring now to the drawings, in which like numerals indicate like elements throughout the several views, FIGS. 1 and 2 illustrate a flexible electrode array 10. The electrode array 10 has an upper end 12, a lower end 14, a front 16, and a back 18. The electrode array 10 comprises an insulating body 20 and a plurality of electrodes 21. Each electrode 21 comprises a conductor 22 preferably largely encapsulated inside the insulating body 20, an exposed electrode recording/stimulating pad 24 at the lower end of the body 20, and an exposed connector portion or bonding pad 25 at the upper end of the body. The electrode array 10 of the disclosed embodiment is 1-100 mm in length, 0.01-0.1 mm in width, and 1-10 microns, preferably approximately 1 micron, in thickness.

With further reference to FIG. 1, the electrode array 10 can be viewed in terms of its function. When thus considered, the array includes a connector area 26 adjacent its upper end 12, an electrode recording/stimulating section 28 adjacent its lower end, and a signal conducting region 30 in its intermediate portion interconnecting the connector area 26 and the electrode recording/stimulating section 28.

For convenience of description the electrode array 10 depicted in the drawings shows only a single pair of electrodes 21. It will be understood that the number of electrodes 21 is not critical and that a greater or lesser number of electrodes can be provided, depending upon the needs of the particular application.

Figure 3:
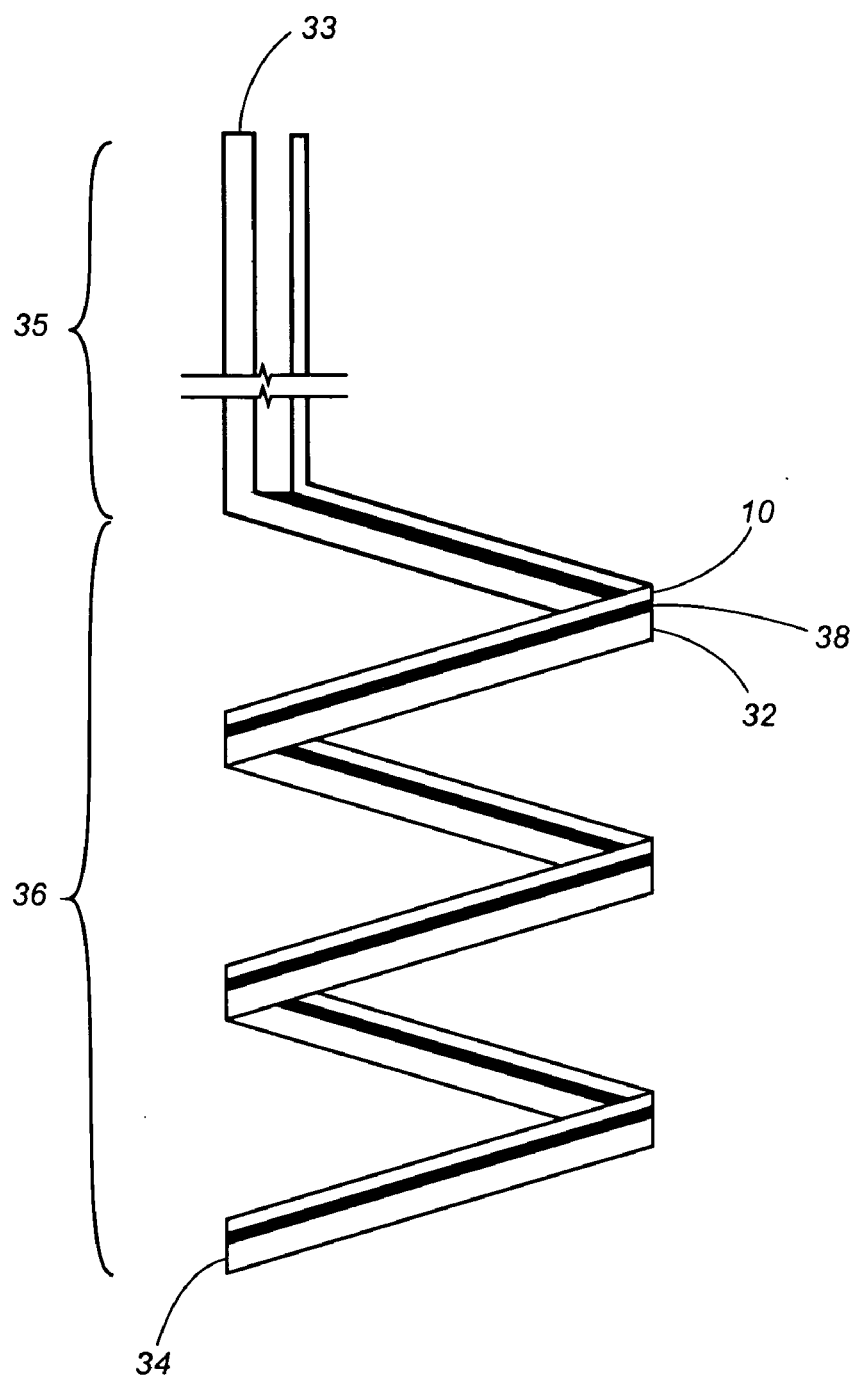
FIG. 3 is a side view of an electrode of FIG. 1 coupled to an introducer.

FIG. 3 shows a flexible electrode array 10 mounted to an introducer 32 for introducing the electrode recording/stimulating section 28 of the array 10 into the tissues of a patient. The introducer 32 comprises a wire having an upper end 33 and a lower end 34. The wire is preferably formed from a shape memory material such as nitinol. The upper portion 35 of the introducer 32 is straight, and a lower portion of the introducer is formed into a helix 36. The electrode array 10 is adhered to the introducer 32 by a layer 38 of a biocompatible, dissolvable adhesive such as mannitol.

FIGS. 4-6 illustrate a method of using the introducer 32 for placement of the electrode recording/stimulating section 28 of the flexible electrode array 10 into the body of a patient. Referring first to FIG. 4, a cannula 40 is inserted into the tissues 42 of a patient. The cannula has an upper end 44 and a lower end 46. To minimize trauma to the tissue 42, the cannula 40 can be of a diameter smaller than the diameter of the helix 36 of the introducer 32. As shown in FIG. 5, with the electrode array 10 attached to the helical introducer 32, the lower end 34 of the introducer is inserted into the upper end 44 of the cannula 40, and the introducer 32 is then rotated in the direction of the helix 36. This rotation causes the helix 36 with electrode array 10 attached thereto to unwind as it advances within the cannula 40. As the lower end 34 of the introducer 32 emerges from the lower end 46 of the cannula 40, the shape memory material of the introducer 32 causes the helix 36 with attached electrode array 10 to resume its coiled configuration within the tissues 42 of the patient.

FIG. 6 shows the introducer 32 and attached electrode array 10 with the helical portion 36 fully coiled within the tissues 42 of the patient. The upper end 33 of the introducer protrudes from the upper end 44 of the cannula 40.

After a period of exposure to fluid within the tissues, the adhesive layer coupling the electrode array 10 to the introducer 32 dissolves. Then, as shown in FIG. 7, the introducer 32 can be rotated in the direction opposite to the turns of the helix 36 to withdraw the introducer from the patient, leaving the electrode array 10 in place. FIG. 8 shows the introducer 32 fully withdrawn from the cannula 40. The cannula 40 can now be withdrawn, leaving the electrode recording/stimulating section 28 of the electrode array 10 coiled within the tissues of the patient.

Figure 9:
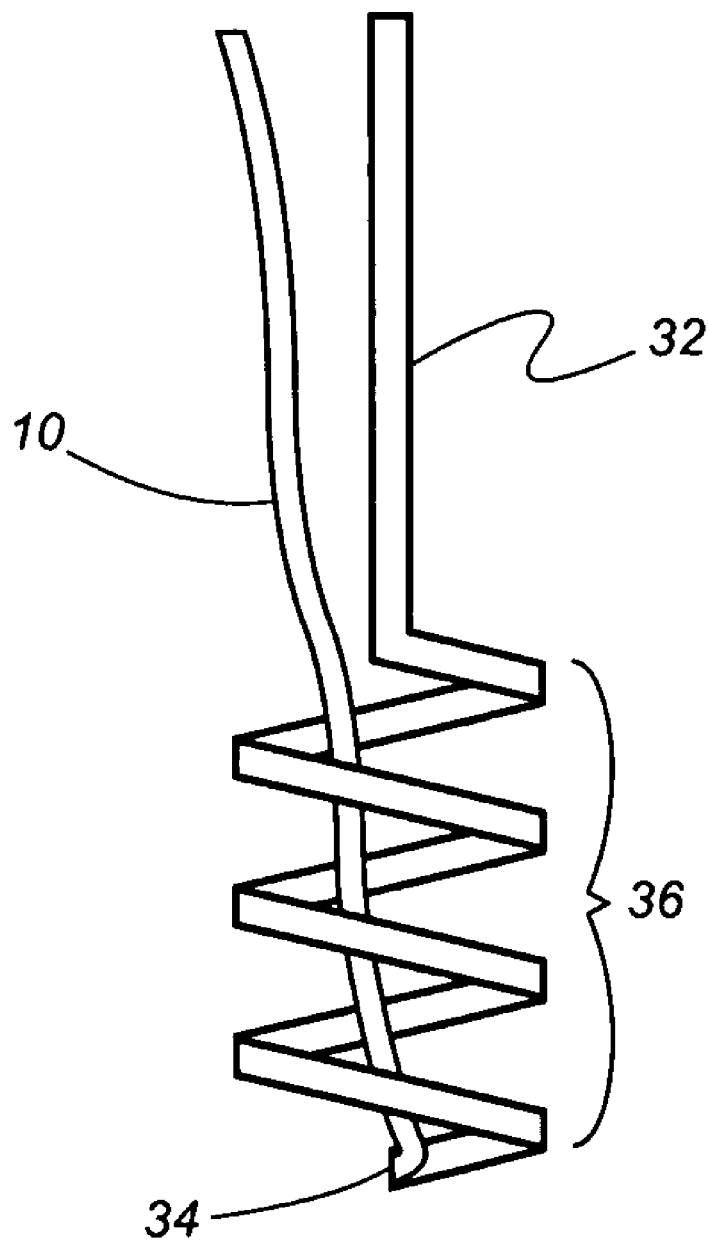
FIG. 9 is a side view of an alternate arrangement of the electrode of FIG. 1 and the introducer of FIG. 3.

FIG. 9 illustrates an alternate arrangement of the electrode array 10 and introducer 32. Rather than attaching the electrode array 10 to the introducer 32 along the entire length of the helical section 36, the electrode 10 is attached only at the tip 34 of the introducer. Attachment can be made by a dissolvable adhesive, as previously explained, or by a suitable one-way mechanical connection that will pull the electrode in a first direction but disengage when the introducer is moved in the opposite direction. When the introducer 32 is helically advanced into the tissues of a patient, the helical portion 36 of the introducer will create a helical track within the tissues. The electrode array 10 is too flexible to make its own track and will thus follow the tip 34 along the helical track created by the introducer. When the introducer 32 is subsequently backed out of the tissue, the electrode array 10 will remain in place.

Figure 10:
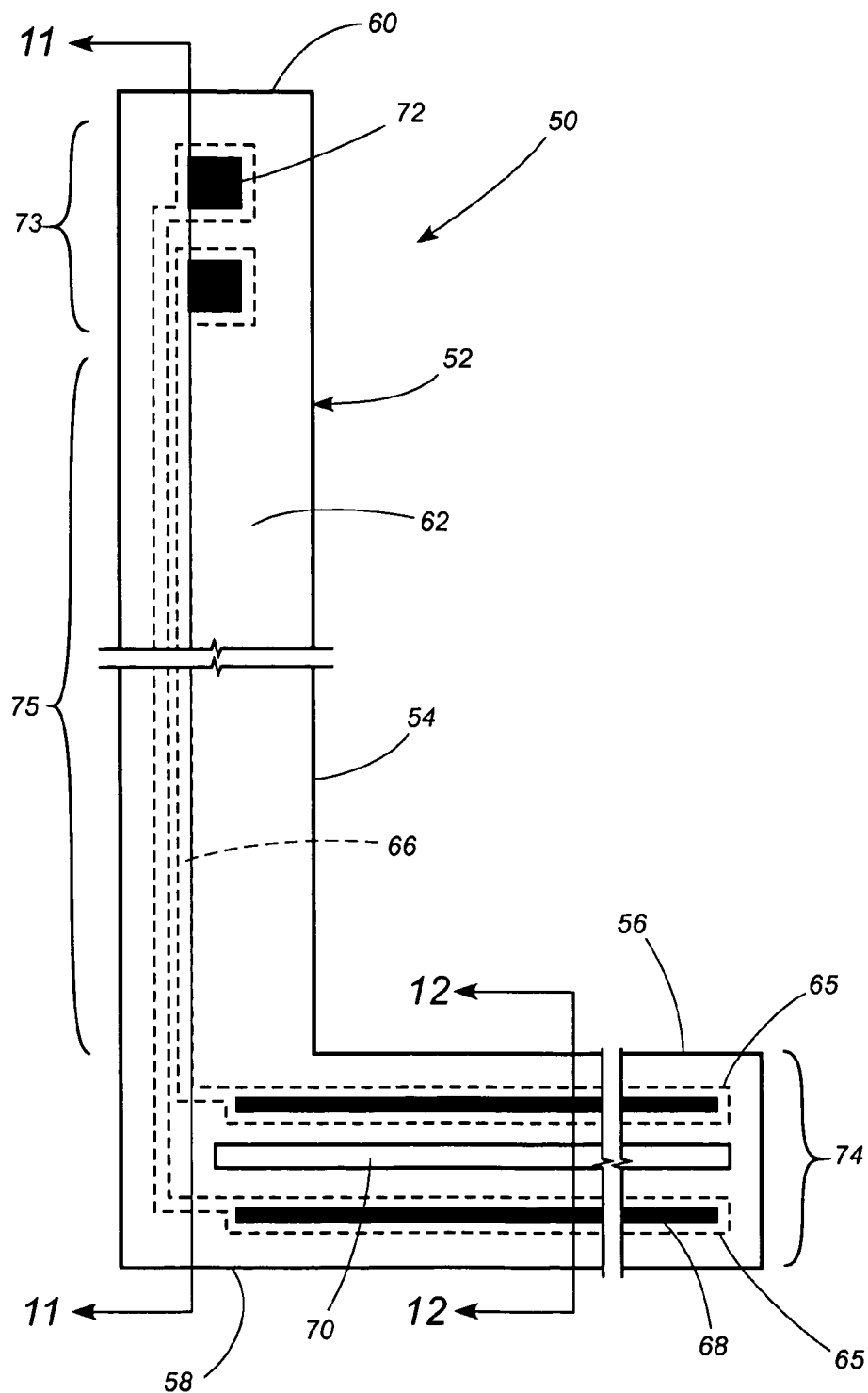
FIG. 10 is a side view of an electrode according to a second disclosed embodiment.

FIGS. 10-12 illustrate an alternate embodiment of an electrode array 50. The electrode array 50 comprises an insulating body 52 having a first section 54 and a second section 56 extending laterally from the lower end 58 the first section 54. The insulating body 52 has an upper end 60, a front 62, and a back 64. The electrode array 50 comprises a pair of electrodes 65. Each electrode 65 comprises a conductor 66 preferably at least largely encapsulated inside the first section 54 of the body 52. Each electrode 65 further comprises an exposed electrode element 68 extending along the second section 56 of the insulating body 52. A conducting gap 70 is formed in the second section 56 of the body 52 between each adjacent pair of electrode elements 68. Exposed connector portions or bonding pads 72 are provided at the upper end of the body 52. The body 52 between the upper end 60 and the lower end 58 is 1-100 mm in length and 0.01-0.1 mm in width. The second section 56 of the body 52 of the disclosed embodiment is 0.1 to 1.0 mm in height and 1.0 to 10.0 mm in length. The electrode array 50 of the disclosed embodiment is 1-10 microns, preferably approximately 1 micron, in thickness.

As with the electrode 10, the electrode 50 can also be defined in terms of its functionality, with a connector area 73 being located adjacent its upper end 60, an electrode recording/stimulating section 74 adjacent its lower end 58, and a signal conducting region 75 in its intermediate portion interconnecting the connector area 73 and the electrode recording/stimulating section 74.

Figure 13:
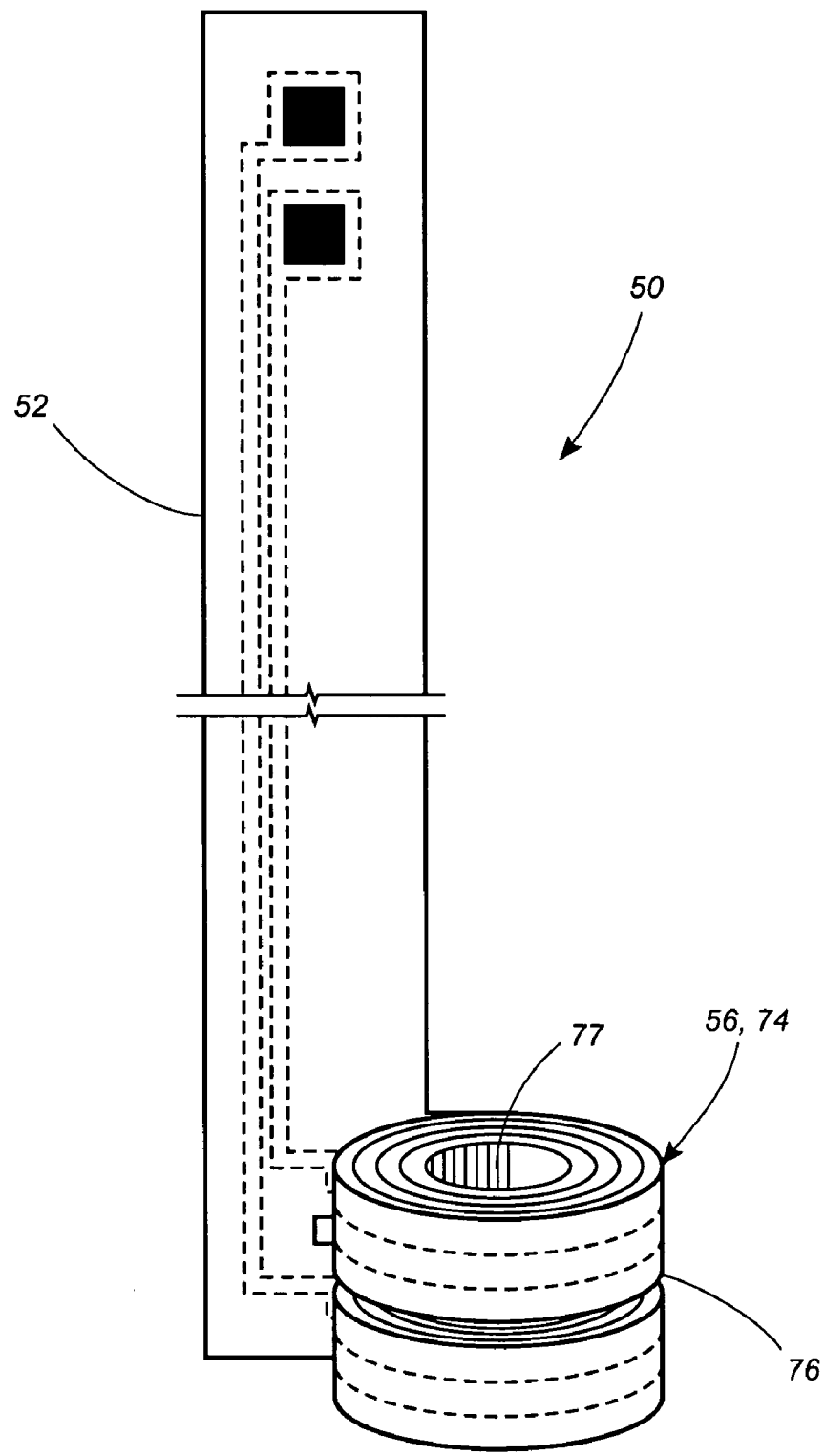
FIG. 13 is a side view of the electrode of FIG. 10 showing the electrode array coiled up into a three-dimensional structure.

In FIG. 13 the second section 56 of the insulating body 52 with exposed electrode elements 68 (not visible in FIG. 13), also known as the electrode recording/stimulating section 74, is wrapped into a cylindrical coil 76. This coil 76 locates the electrode elements 68 in a three-dimensional matrix. The innermost turn of the coil 76 is loosely wrapped such that a hole 77 is formed in the center of the coil.

Figure 14:
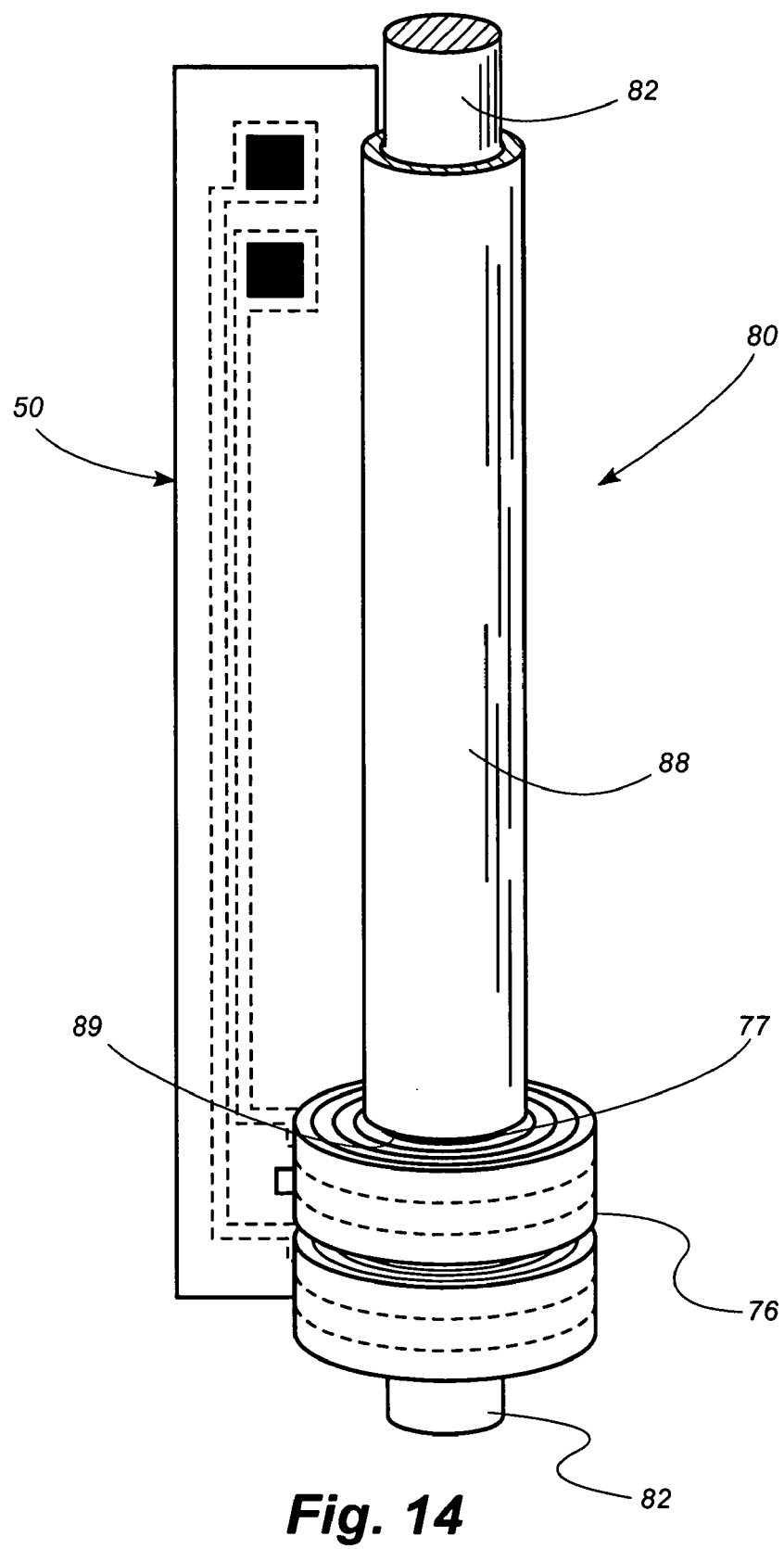
FIG. 14 is a side view of an apparatus for implanting the device of FIG. 1 into the tissues of a patient.

FIG. 14 depicts an assembly 80 for introducing the coil 76 of the electrode array 50 into the tissues of a patient. An electrode array 50 has its electrode recording/stimulating section wrapped into a cylindrical coil 76, as previously described. A guide wire 82 of indeterminate length extends through the hole 77 in the center of the coil 76. A length of hypodermic tubing 88 is telescopically disposed over the guide wire. The length of hypodermic tubing 88 has an outer diameter larger than the hole 77 in the center of the coil 76 such that the lower end 89 of the tubing abuts the upper surface of the coil 76.

Figure 15:
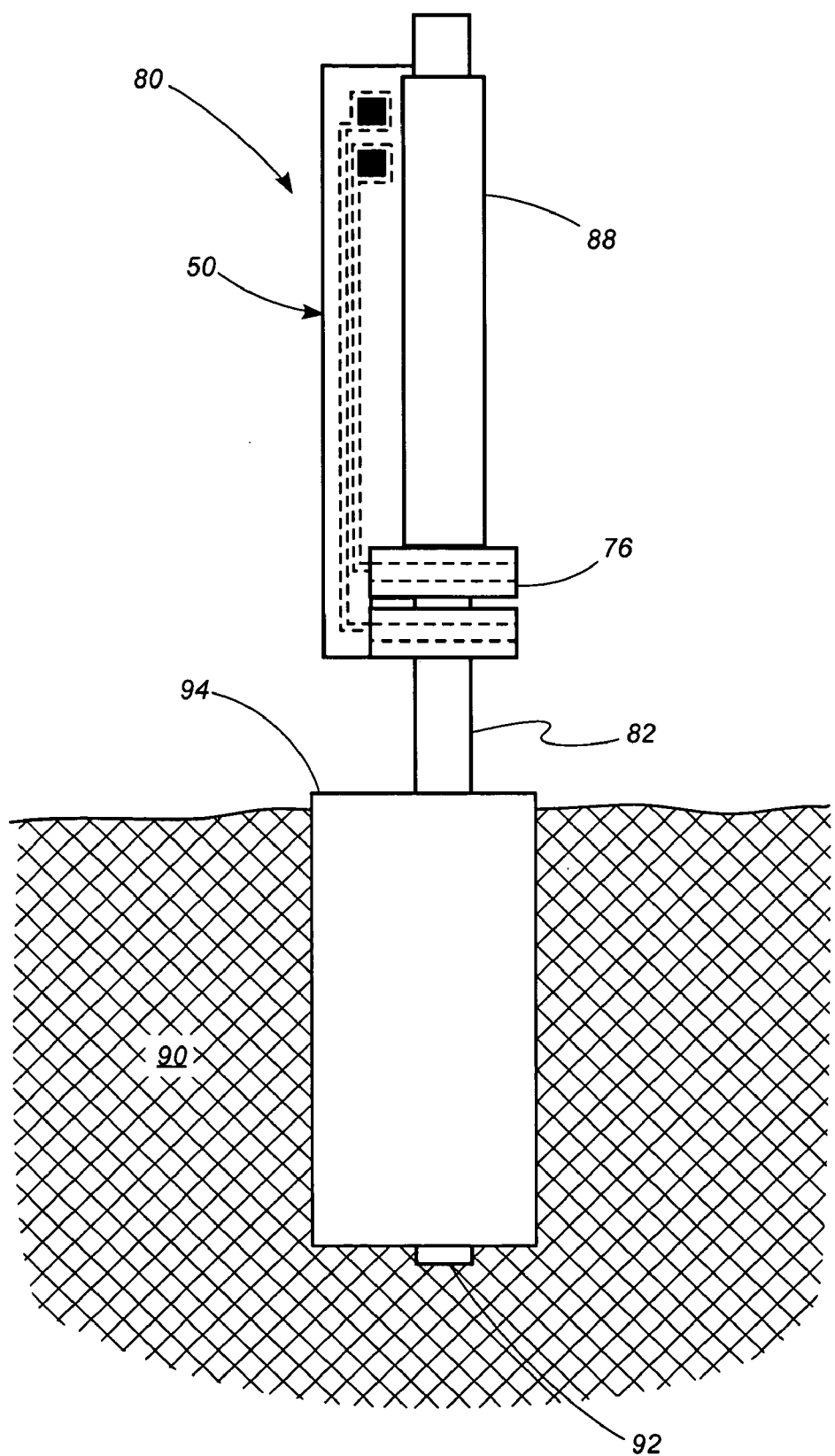
FIGS. 15-19 are side views illustrating the implantation of the electrode of FIG. 10 within the tissues of a patient.

FIGS. 15-19 illustrate a procedure for use of the device 80 to introduce the coil 76 of the electrode array 50 into the tissues 90 of a patient. Referring first to FIG. 15, the guide wire 82 is introduced into the tissues 90 and advanced under appropriate imaging technology until the forward tip 92 of the guide wire 82 is located proximate to the target site. A cannula 94 is then inserted over the guide wire 82. The proximal end of the guide wire 82 is threaded through the hole 77 in the center of the coil 76 of the electrode 50. The length of hypodermic tubing 88 is advanced over the proximal end of the guide wire until it abuts the coil 76. Thereafter further advancement of the hypodermic tubing 88 pushes the electrode 50 along the guide wire 82.

Figure 16:
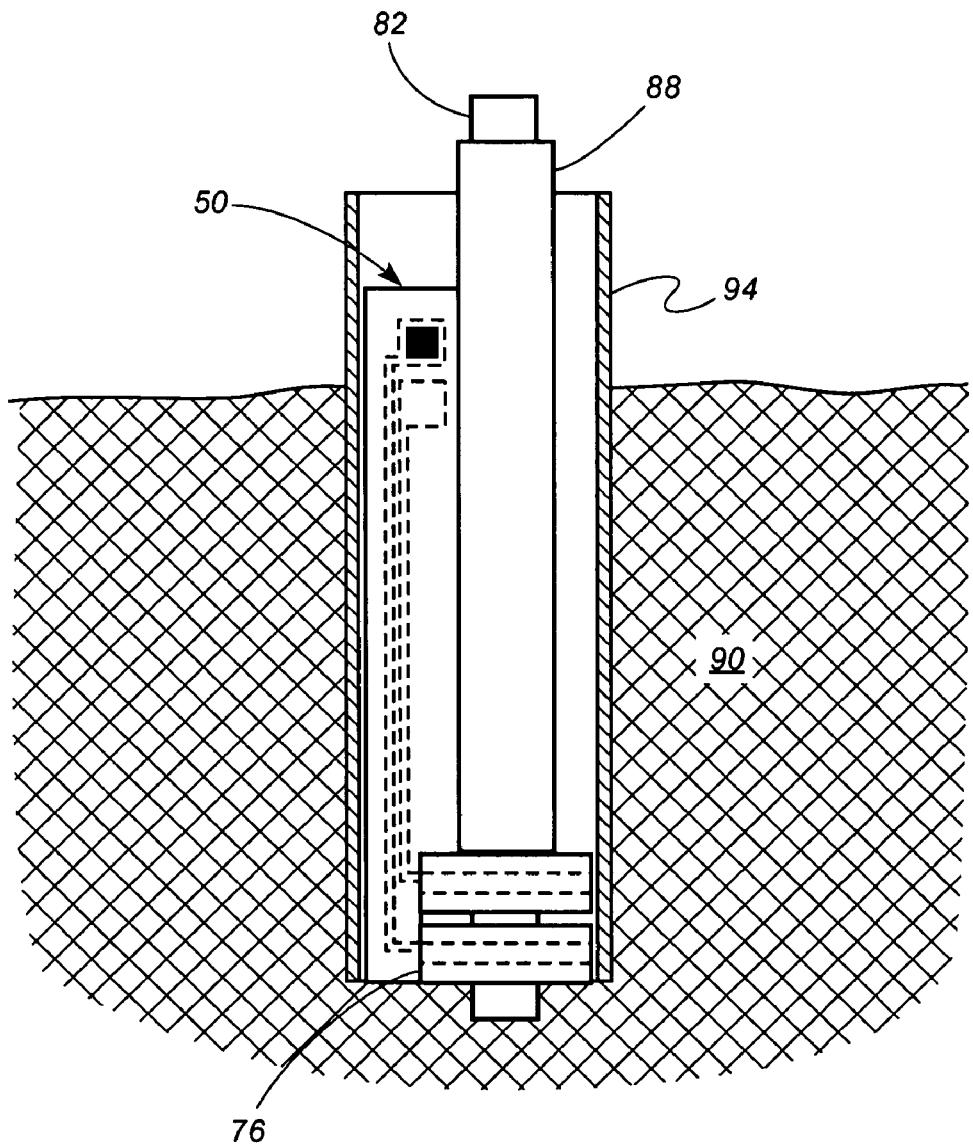
Figure 17:
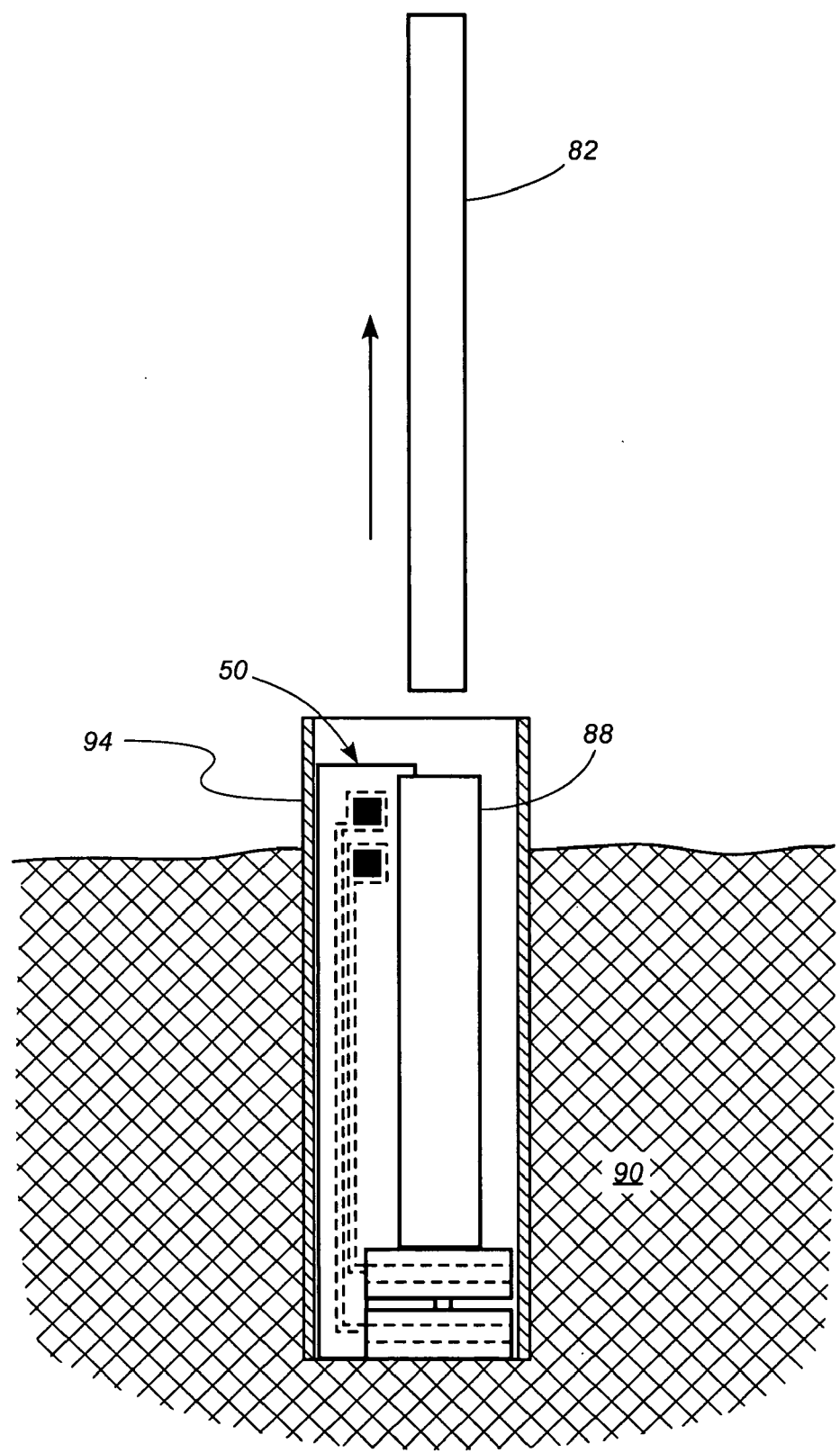
Figure 18:
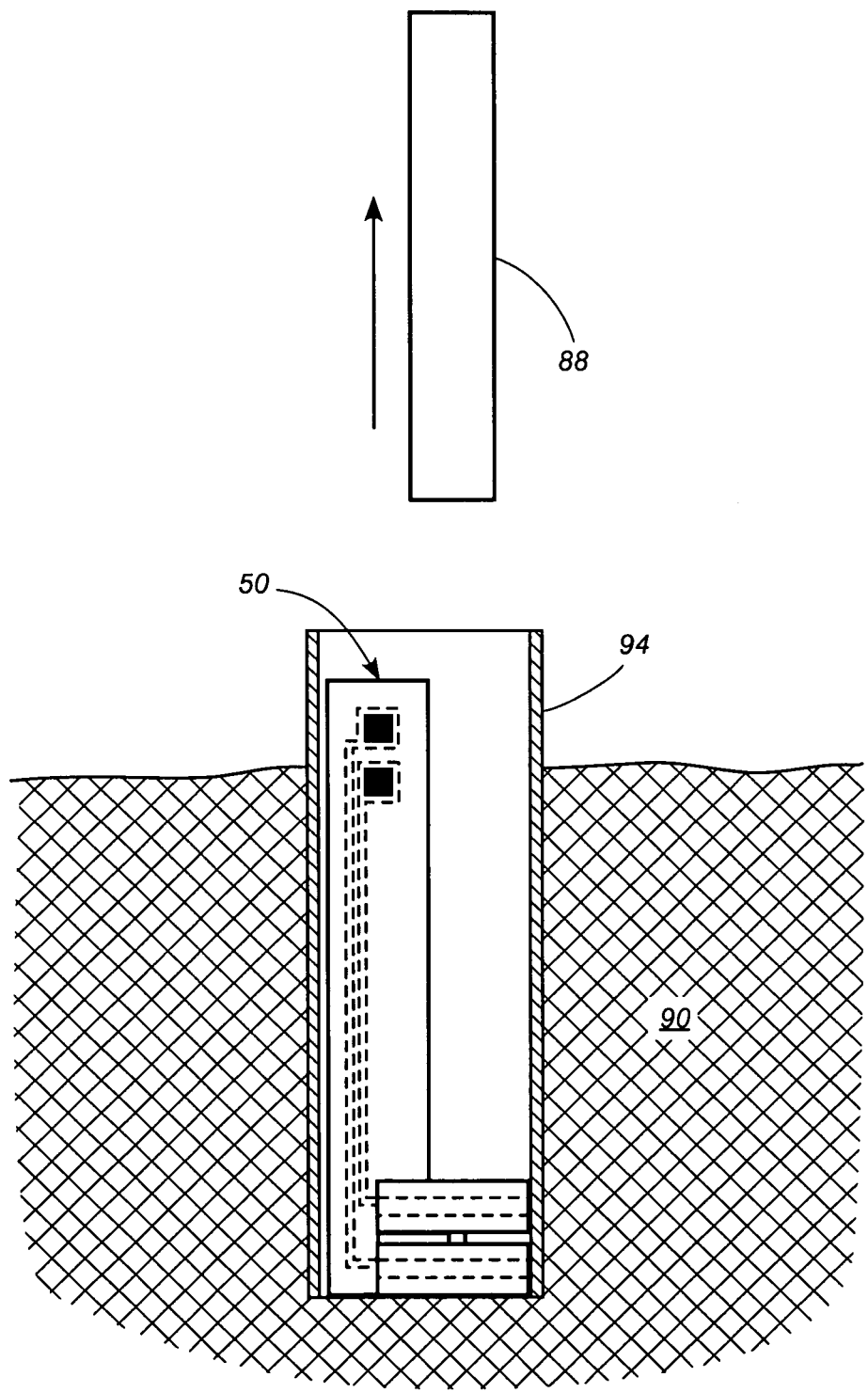
Figure 19:
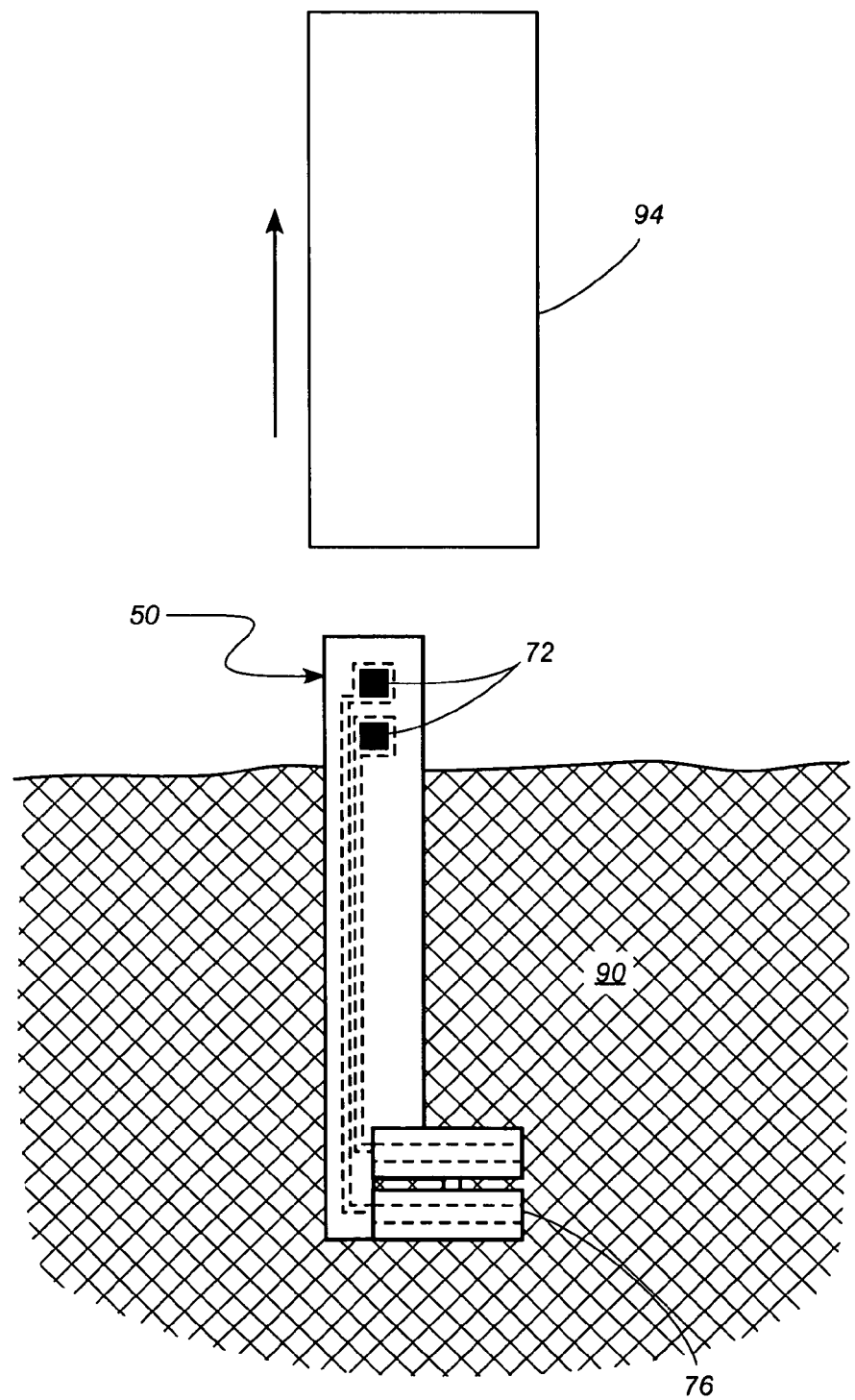

As shown in FIG. 16, the hypodermic tubing 88 is used to advance the electrode array 50 along the guide wire 82 until the coil 76 of the electrode array is located within the target site. At this point, the guide wire 82 and hypodermic tubing 88 are removed, as shown in FIGS. 17 and 18, and the cannula 94 is withdrawn, as shown in FIG. 19, leaving the coil 76 of the electrode 50 positioned within the tissues 80 of the patient. The bonding pads 72 are disposed outside the patient's body to enable the electrode array 50 to be electrically connected to external electronics for stimulating or detecting electrical activity within the tissue 90.

Figure 20:
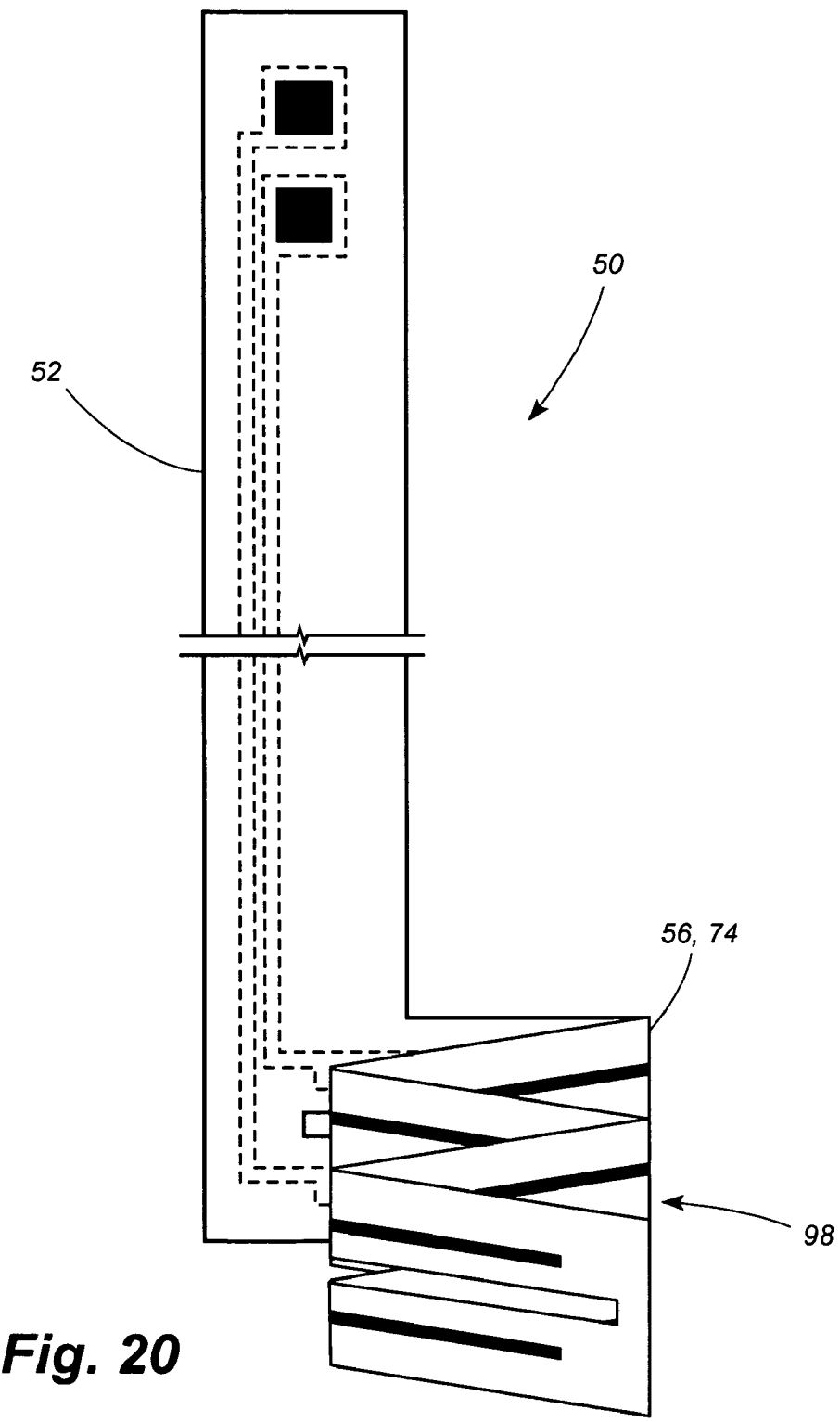
FIG. 20 is a plan view of the electrode of FIG. 10 showing the electrode array folded up into a three-dimensional structure.

The purpose of coiling the electrode recording/stimulating section 74 of the electrode array 50 into a cylinder is to locate the electrodes in a three-dimensional arrangement, as opposed to the substantially linear arrangement of the electrode recording/stimulating section 24 of the electrode array 10. However, it will be appreciated that other methods of placing the electrode recording/stimulating section 24 of the electrode array 10 in a non-linear path may be implemented, such as folding the section 24 over onto itself a number of times to create a substantially box-shaped array 98 (see FIG. 20).

Manufacture of the electrode array 10 will now be explained with reference to FIGS. 21-37.

Figure 21:
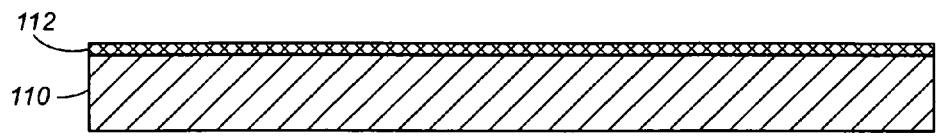

In FIG. 21, a substrate 110 receives a deposited layer of an insulating material 112. In the disclosed embodiment, the substrate is glass, quartz, silicon. Also in the disclosed embodiment, the insulating material is polyimide deposited in a layer 200-500 nanometers thick.

Figure 22:
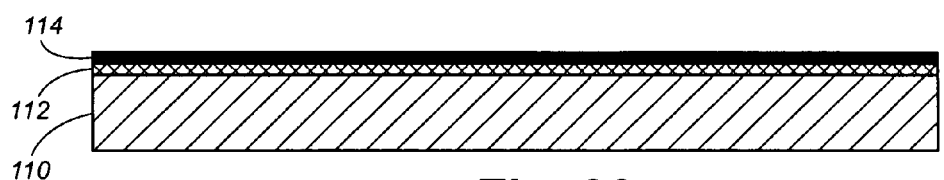

In FIG. 22, a layer of conducting material 114 has been deposited atop the layer of insulating material 112. In the disclosed embodiment, the layer of conducting material is gold, platinum, or other noble metal approximately 200-500 nanometers thick.

Figure 23:
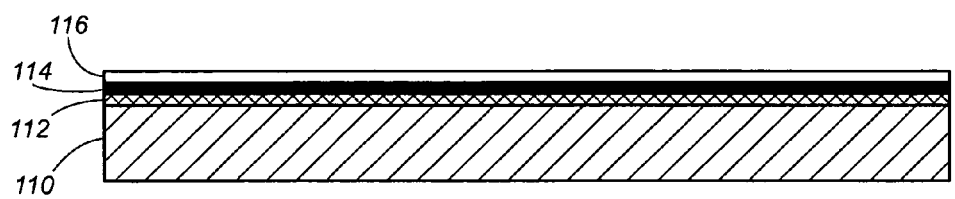

FIG. 23 shows a layer of photoresist material 116 deposited on top of the layer of conducting material 114. In the disclosed embodiment, the photoresist material is deposited in a layer 200 nanometers thick.

Figure 24:
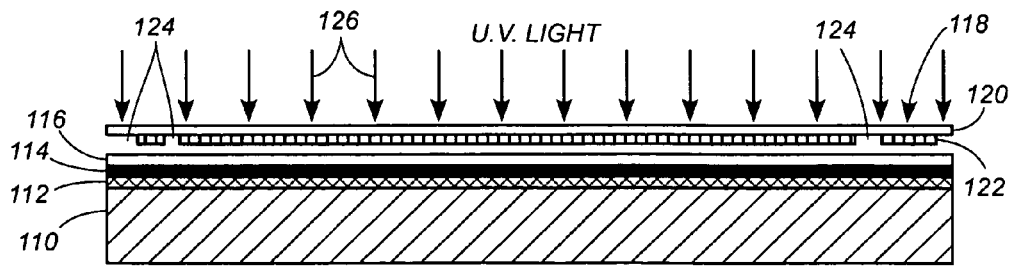

Referring now to FIG. 24, an optical mask 118 comprises a translucent backing sheet 120 and opaque masking areas 122. Openings 124 are formed in the opaque masking areas 122. The optical mask 118 is positioned above the photoresist layer 116. UV light 126 is then directed onto the optical mask 118 such that it shines through the openings 124 in the opaque masking areas 122 and onto the photoresist layer 116 beneath.

Figure 25:
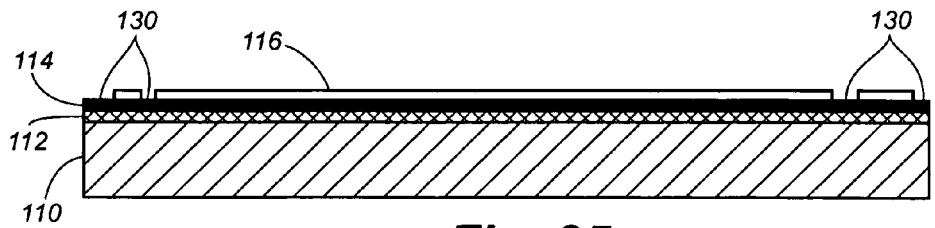

In FIG. 25, the photoresist layer 116 has been chemically developed to remove those areas 130 that have been exposed to the UV light.

Figure 26:
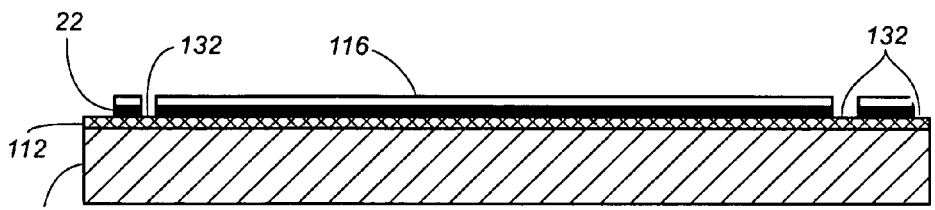

In FIG. 26 a chemical etching agent is applied onto the chemically developed photoresist layer 116. The chemical etching agent etches apertures 132 in the conducting material 114 through the apertures 130 in the developed photoresist layer 116. Upon completion of the chemical etching process, the conducting material 114 is now the finished conductors 22.

Figure 27:
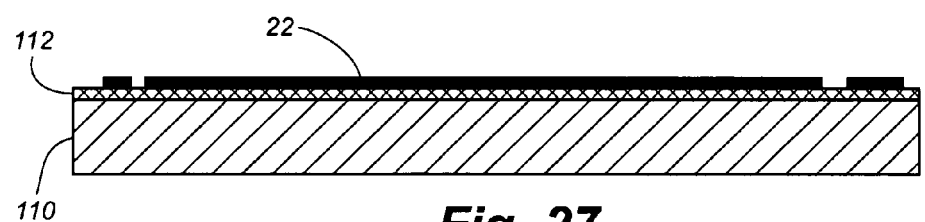

FIG. 27 illustrates that the photoresist layer 116 has been removed from the top of the conductors 22. In the disclosed embodiment the removal is accomplished by placing the assembly in, e.g., acetone.

Figure 28:
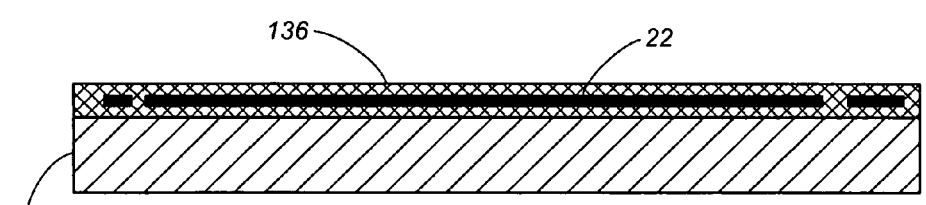

In FIG. 28, additional insulating material has been deposited onto and around the conductors 22 to create a layer 136 that extends above the tops of the conductors. Again, in the disclosed embodiment the insulating material is polyimide.

Figure 29:
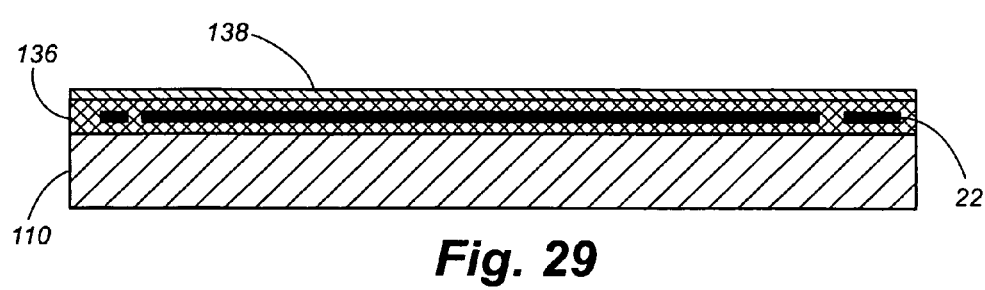
Figure 30:
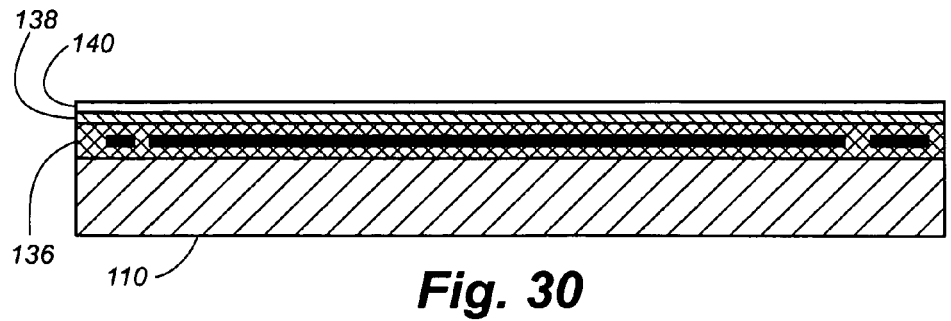

In FIG. 29, a mask 138 for plasma etch has been deposited on top of the layer 136 of insulating material. FIG. 30 shows a layer of photoresist 140 added atop the mask 138.

Figure 31:
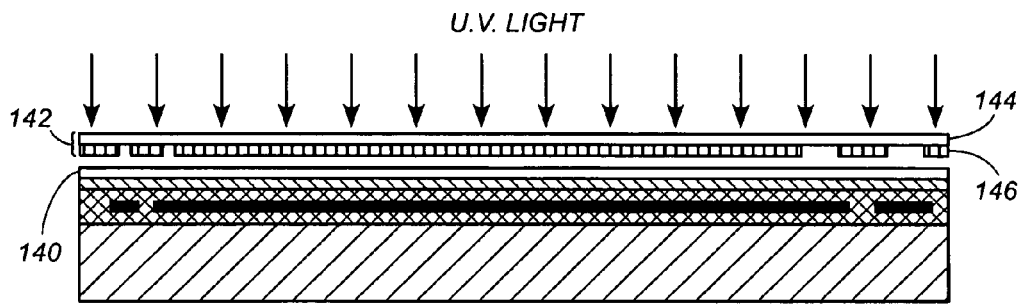

In FIG. 31, an optical mask 142 comprising a translucent backing sheet 144 and opaque masking areas 146 is positioned above the photoresist layer 140. UV light is then directed onto the optical mask 142 such that it shines through the areas between the opaque masking areas 146 and onto the photoresist layer 140 beneath.

Figure 32:
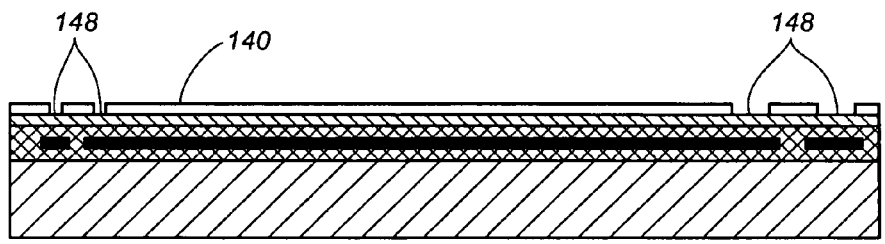

Referring now to FIG. 32, the photoresist layer 140 has been chemically developed to remove those areas 148 that have been exposed to the UV light, thereby exposing selected portions of the insulating layer 136.

Figure 33:
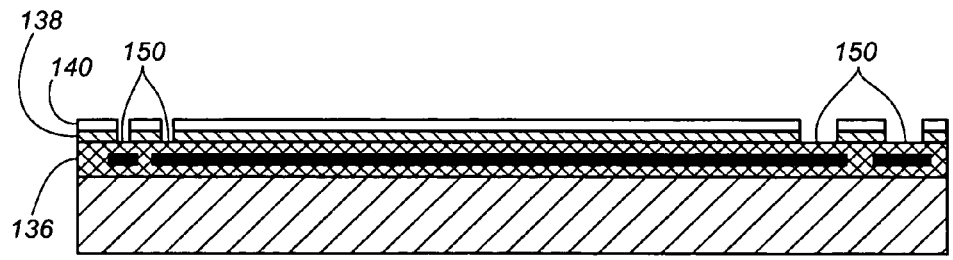

In FIG. 33, a chemical etching agent has been applied onto the chemically developed photoresist layer 140. The chemical etching agent etches the mask for plasma etch 142 through the apertures 148 (FIG. 32) in the developed photoresist layer 140. Upon completion of the chemical etching process, the mask for plasma etch 142 comprises apertures 150 formed therethrough.

In FIG. 34 the photoresist layer 140 (see, e.g., FIG. 33) has been removed to expose the mask 138 with apertures 150 formed therethrough. In FIG. 35, the insulating layer 136 is etched with plasma through the apertures 150 in the mask 138. This plasma etching process removes selected portions of the insulating layer 136 to expose the electrodes 24 and bonding pads 25.

In FIG. 36 the mask 138 for plasma etch (see, e.g., FIG. 34) has been removed to expose the upper surface of the insulating layer 136.

FIG. 37 shows the finished electrode array 10 removed from the substrate 110.

Unless otherwise stated, terms used herein such as "top," "bottom," "upper," "lower," "left," "right," "front," "back," "proximal," "distal," and the like are used only for convenience of description and are not intended to limit the invention to any particular orientation.

Finally, it will be understood that the preferred embodiment has been disclosed by way of example, and that other modifications may occur to those skilled in the art without departing from the scope and spirit of the appended claims.

What is claimed is:

1. An apparatus comprising:

A flexible electrode body having an upper end an opposed lower end and defining a first opening and a second opening;

a shaped deformable introducer wire having an upper portion and an opposed lower portion, wherein the upper portion of the introducer wire is substantially straight and the lower portion of the introducer wire is configured as a helix, and wherein the electrode body has a relaxed configuration and is resiliently deformable to pass through a cannula and at least partially resume the relaxed configuration when placed within a patient's tissue;

a means for removably attaching the electrode to the introducer wire such that the introducer wire can embed the flexible electrode body in a three-dimensional configuration within the patient's tissue and can then be removed from the patient's tissue, leaving the electrode body in situ; and at least one electrode, wherein the electrode comprises:

an electrode pad at the lower end of the electrode body, a connector pad at the upper end of the electrode body, and a conductor directly electrically connecting said electrode pad and said conductor pad, said conductor pad being enclosed within said body;

wherein the first opening in said electrode body is positioned in registry with said electrode pad so as to expose said electrode pad to the patient's tissue, and wherein the second opening in said electrode body is positioned in registry with said connector pad so as to expose said connector pad for connection to external electronics.

2. The apparatus of claim 1, wherein said electrode body comprises a first flexible sheet in contact with a second flexible sheet.

3. The apparatus of claim 2, wherein at least one of the first sheet and the second sheet comprises polyimide.

4. The apparatus of claim 2, wherein said conductor is interposed between portions of said first and second flexible sheets and wherein said conductor is encapsulated by the respective first and second flexible sheets.

5. The apparatus of claim 4, wherein said electrode body has a cross-sectional thickness of from approximately 1 micron to approximately 10 microns.

6. The apparatus of claim 1, wherein at least a portion of the electrode body has a helical shape.

7. The apparatus of claim 1, wherein the at least one electrode comprises a first electrode and a second electrode.

8. The apparatus of claim 1, wherein the at least one electrode comprises a plurality of electrodes.

* * * * *